United States Patent [19]

Stasz et al.

[11] Patent Number: 4,958,539
[45] Date of Patent: Sep. 25, 1990

[54] METHOD OF MAKING AN ELECTROSURGICAL SPATULA BLADE

[75] Inventors: Peter Stasz, Moundsview; Jeffrey J. Solberg, Northfield; Scott R. Grabinger, Maple Grove, all of Minn.

[73] Assignee: Everest Medical Corporation, Brooklyn Center, Minn.

[21] Appl. No.: 360,856

[22] Filed: Jun. 2, 1989

Related U.S. Application Data

[62] Division of Ser. No. 161,776, Feb. 29, 1988, Pat. No. 4,862,890.

[51] Int. Cl.$^5$ .............................................. B21K 11/00
[52] U.S. Cl. ...................... 76/104.1; 65/60.4; 65/61; 65/62; 76/101.1; 204/192.15; 29/527.2
[58] Field of Search ................... 65/61, 62, 60.4; 30/346.53, 346.54, 346.55, 350; 76/104.1, 101.1; 29/527.2

[56] References Cited

U.S. PATENT DOCUMENTS

| | | | |
|---|---|---|---|
| 3,761,372 | 9/1973 | Sastri | 204/192.15 |
| 3,761,373 | 9/1973 | Sastri | 204/192.15 |
| 3,761,374 | 9/1973 | Bromer et al. | 76/104.1 X |
| 3,811,189 | 5/1974 | Sastri | 30/346.53 |
| 4,770,067 | 9/1988 | Liu et al. | 76/104.1 |
| 4,802,476 | 5/1989 | Nuerenberg et al. | |

FOREIGN PATENT DOCUMENTS 2160102 12/1985 United Kingdom .

Primary Examiner—Carl E. Hall
Assistant Examiner—Carl J. Arbes
Attorney, Agent, or Firm—Orrin M. Haugen; Thomas J. Nikolai; Frederick W. Niebuhr

[57] ABSTRACT

A surgical cutting blade for use in an electrosurgical scalpel includes a thin flat ceramic substrate having a rounded tip where the edge portion of the substrate on the opposed major surfaces thereof are beveled. A pattern of metallization is provided on the opposed major surfaces of the blade substrate with the metallization extending over the tapered portions. The substrate is then back-ground to form a blunt edge extending between the tapered surfaces at the edge of the substrate. The metallization pattern further includes traces extending from the conductors along the blunt working edge of the blade to the handle receiving portion thereof and provide a means whereby RF energy may be conducted to the metallized working edge of the blade.

3 Claims, 2 Drawing Sheets

METHOD OF MAKING AN ELECTROSURGICAL SPATULA BLADE

This is a Divisional of application Ser. No. 07/161,776, filed Feb. 29, 1988 now U.S. Pat. No. 4,662,890 issued 9/5/89.

BACKGROUND OF THE INVENTION

I. Field of the Invention

This invention relates generally to electrosurgical apparatus, and more particularly to a blade adapted to be used as an electrosurgical scalpel for parting tissue using radio-frequency energy.

II. Discussion of the Prior Art

In a co-pending application Ser. No. 56,434, filed June 1, 1987 now U.S. Pat. No. 4,802,476 issued May 7, 1989, entitled "ELECTROSURGICAL INSTRUMENT" and which is assigned to the assignee of the present invention, there is described an electrosurgical instrument comprising a blade and a blade handle in which the blade is adapted to snap into the handle, and when so positioned, establishes an electrical connection between an RF power source and metallized electrode surfaces formed on the blade. In that application, the blade is fabricated from a metal blank, the metal being overlaid on each side with a suitable insulation, and deposited atop the insulation layers are printed conductors. When the blade is appropriately energized, an RF field is established between the printed conductors and the metal blank. This style of blade is not altogether satisfactory, due primarily to blade erosion. The radio-frequency arc discharge between the printed conductors on the blade and the blade blank itself causes pitting, leading to a relatively short blade life.

In accordance with the present invention, the blade blank is a thin ceramic substrate having a proximal handle receiving segment and an integrally formed distal segment, which is preferably somewhat triangular in shape, but with a rounded apex at its distal end. A portion of the blank, including the adjacent sides and the rounded tip, are beveled at a predetermined angle to the plane of the blank and, during manufacture, a metallization pattern is vacuum-deposited or otherwise formed onto the major surfaces of the blade so as to extend over the beveled surfaces The blank with the metallization on it is then subjected to a backgrinding operation to form a blunt working edge which is free of metallization and which maintains a predetermined spacing between the conductive patterns on the opposed side surfaces of the blank.

The ceramic substrate permits higher temperatures to be used without destruction of the blade surface, thus leading to a longer blade life as compared to those having a metal blank. The ceramic substrate also lends itself to metal deposition processes now commonly available and widely used in the fabrication of integrated hybrid circuits.

In accordance with one embodiment of the invention, the pattern of metallization on the ceramic blank creates an open loop overlaying the beveled edges of the blank. This open loop is then connected by an integrally formed trace extending to the proximal end portion of the blade where it mates with the electrical connector in the blade handle. By providing an open loop tip, the overall capacitance of the blade is reduced, thus reducing the amount of energy wasted in the delivery of power to the load.

In accordance with another aspect of the invention, rather than providing a metallization pattern including a loop conductor, the beveled surfaces of the blank are, instead, entirely covered with metallization. This has the advantage of providing improved heat conductivity away from the blade edge and through the metal trace to a suitable heat sync. As such, the metallization does not become overheated which could result in unwanted melting of the metallization pattern or the oxidation thereof.

Irrespective of the metallization pattern employed, the blade of the present invention may be subjected to a further processing operation prior to the backgrinding of the edges in which a glass-like layer of insulation is provided as an overcoat to the blade blank and the previously applied metallization pattern. By proper choice of the overcoat material, it is possible to minimize adhesion of the blade to tissue during its use. An overcoat possessing good thermal insulation and high impedance characteristics results in much improved performance of the blade in its electrosurgical use.

OBJECTS

It is accordingly a principal object of the invention to provide an improved electrosurgical blade construction.

Another object of the invention is to provide an electrosurgical blade utilizing a ceramic substrate and a predetermined pattern of metallization for enhancing the electrical properties of the blade.

Yet another object of the invention is to provide an electrosurgical blade with improved thermal characteristics and field concentrations over the working edge of the blade.

The foregoing features and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENTS

Figure 1A:
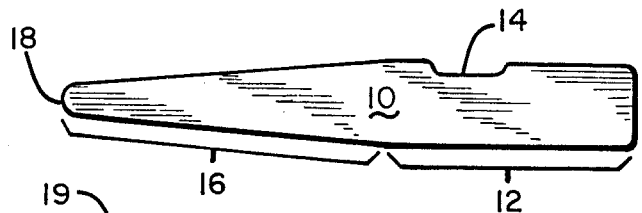
FIGS. 1A–1E illustrate the steps involved in fabricating an electrosurgical blade in accordance with a first embodiment of the invention.
Figure 1B:

Referring first to FIG. 1, there is illustrated by the views A through E the sequence of steps carried out in fabricating an electrosurgical blade in accordance with a first preferred embodiment. In view A of FIG. 1, there is shown a front elevation of a spatula blade blank 10 and is preferably formed by injection molding a green ceramic and then firing the molded part. The blade blank or substrate is seen to include a generally rectangular proximal portion 12 having a notch 14 formed inwardly from one side edge thereof. As is set out in the aforereferenced co-pending application Ser. No. 56,434, the portion 12 is arranged to fit into a blade-receiving handle (not shown) with the notch 14 providing a locking feature.

Integrally formed with the proximal portion 12 is a generally triangular distal end portion 16 having a rounded distal tip 18 at the apex of the triangle.

Typically, but without limitation, the overall length of the blank may be approximately 2.28 inches and the overall thickness may be 0.025 inches. The length of the generally rectangular proximal end portion 12 may be 0.96 inches.

The ceramic material employed may be zirconia, but silicon nitride may be found equally suitable.

Figure 1C:
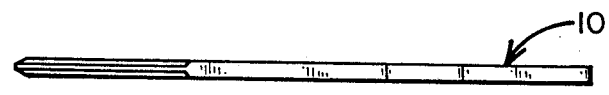
Figure 1D:
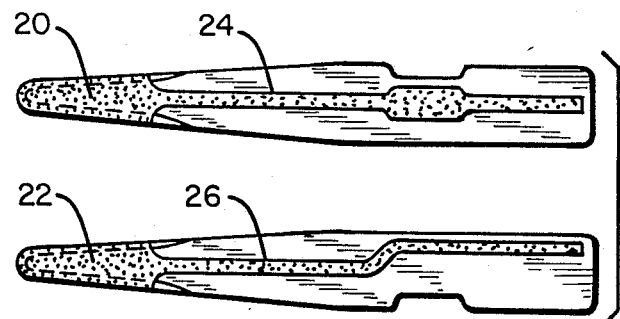
Figure 1E:
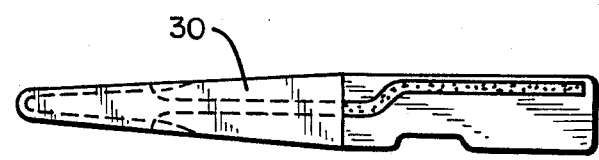
Figure 2:
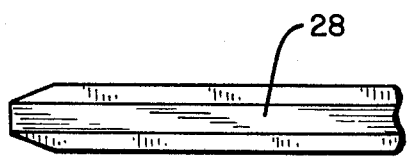
FIG. 2 is an enlarged side view of a portion of the blade of FIG. 1.

Referring next to View B in FIG. 1, the blank 10 is next subjected to a grinding operation whereby the two adjacent legs of the triangular portion 16 and the included tip 18 are tapered or beveled at an angle of approximately 20° to the plane of the blank as shown in the enlarged detail of the edge view of FIG. 1C shown in FIG. 2. This enlarged detail also shows that the beveled surfaces do not meet in a sharp razor-like edge but, instead, the edge is blunt, having a thickness of about 0.003 inches.

Following the grinding operation in which the tapered edges are formed on the opposed major surfaces of the blank 10, the blank is subjected to one or more steps whereby a pattern of metallization is deposited on each major surface of the blank as a substrate. The views labeled D in FIG. 1 show the metallization pattern on the opposed side surfaces of the blank 10. Using a silk screening process, a layer of gold or silver or molybdenum is deposited onto the blank. View D of FIG. 1 includes a portion identified by numerals 20 and 22 entirely covering the portion of the blade over which the tapered or beveled edge 19 of view B is formed. Conductive lines 24 and 26 of relatively narrow width lead back from the metallized tip portions 20 and 22 to the proximal end portion 12 of the blade blank where those lines are intended to mate with electrical contacts formed in the blade handle.

Referring next to FIG. 1E, the blade may next be subjected to an optional coating step wherein the distal end portion 16 of the blade is provided with a dielectric overcoat, such as a glassy material, which, in use, tends to minimize adherence of the blade to tissue. The overcoat should possess the properties of being a good thermal insulator while exhibiting a high impedance which will preclude current from exiting through the side walls of the blade. Suitable candidates for the glass overcoat may be silicon oxide, aluminum oxide, silicon nitride, boron nitride or zirconium oxide. In view E of FIG. 1, the overcoat material is identified by numeral 30.

Once the metallization and the optional overcoating steps have been completed, the blade is then subjected to a backgrinding operation which insures that the blunt edge portion 28 (FIG. 2) is stripped free of any traces of metal which might create a low impedance path from the metallization pattern on one side of the blade to that on the other.

Figure 3A:
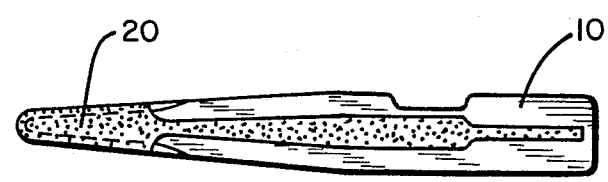
FIGS. 3A and 3B illustrate the metallization pattern on an electrosurgical blade in accordance a second embodiment of the invention.
Figure 3B:
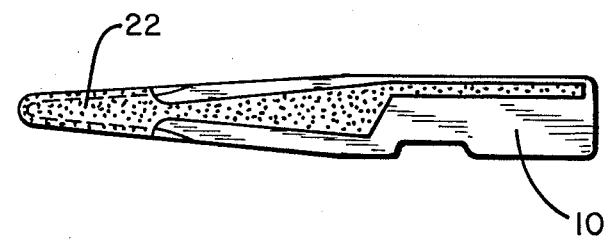

Referring next to FIG. 3, the views A and B illustrate a modification to the metallization pattern employed in step D of FIG. 1. The distal tip portions 20 and 22 are again totally covered with metallization, but rather than having a thin conductive strip like strips 24 and 26 in view D of FIG. 1, the width dimension of the metallization leading from the tip to the proximal end of the blade is significantly greater on both major surfaces of the blank 10. This increased area of metallization has the effect of conducting heat energy away from the working tip. Tissue cutting is a result of the RF energy passing through the tissue as the arc spans the gap form the conductive pattern 20 on one side of the blade to the conductive pattern 22 on the opposed side. The ceramic substrate becomes sufficiently heated to cauterize the severed blood vessels but without undue burning.

Figure 4A:
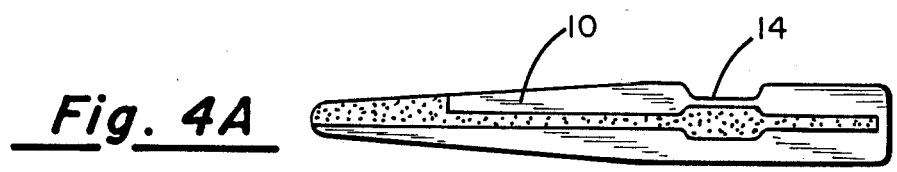
FIGS. 4A and 4B illustrate the pattern of metallization on an electrosurgical blade in accordance with a second alternative embodiment.
Figure 4B:
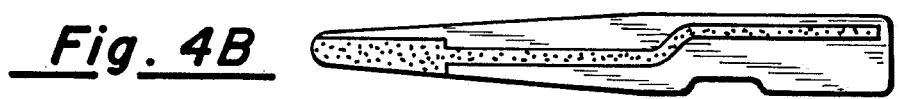

In FIG. 4, Views A and B show a variation in the metallization pattern so that only about one-half of the distal tip portion of the blade show in FIG. 3 is metallized, yielding a blade with only a single cutting edge area thereon.

Figure 5A:
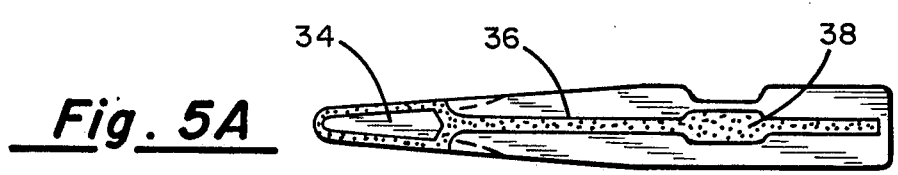
FIGS. 5A and 5B illustrate the pattern of metallization on an electrosurgical blade in accordance with another alternative embodiment.
Figure 5B:
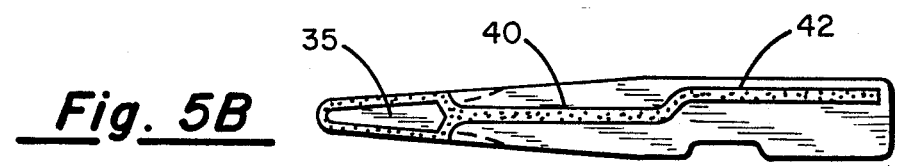

FIG. 5 shows an alternative metallization pattern wherein primarily only the beveled surface of the tip portion of the blank is metallized, thus forming a loop as at 34. The metallization pattern including the loop 34 is joined by a Y-shaped trace 36 to a pad area 38 formed on one major surface (View A). As is explained in the aforereferenced co-pending patent application, the conductive area 38 is intended to mate with a piezoelectric crystal contained in the blade handle, the crystal imparting high frequency vibration to the blade member whereby the buildup of tissue debris on the blade is, to a large extent, obviated.

View B of FIG. 5 shows the obverse side of the blade blank from that shown in view A. It, too, includes a Y-shaped trace 40 leading to a contact area 42 on the proximal, handle-receiving portion of the blade. Because the traces 36 and 40 are relatively narrow, they conduct less thermal energy away from the tip's loop conductor while permitting the high RF voltage to be developed across the loop conductors on opposed major surfaces of the blade blank.

Figure 6A:
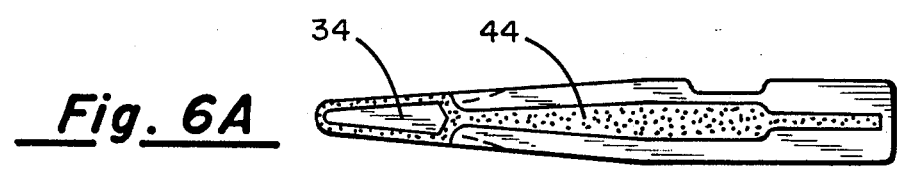
FIGS. 6A and 6B illustrate the pattern of metallization in an electrosurgical blade in accordance with another alternative embodiment.
Figure 6B:
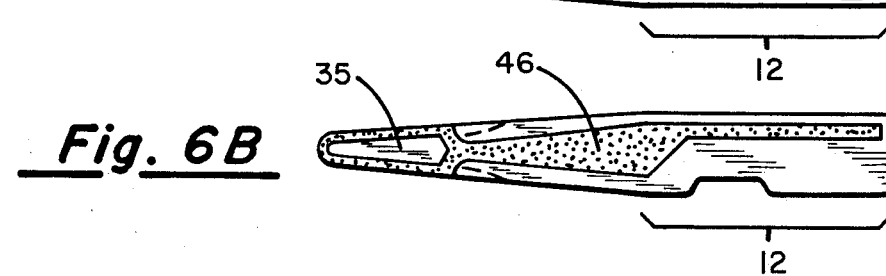

FIG. 6 shows still another alternative metallization pattern for an electrosurgical blade. The arrangement of FIG. 6, like that in FIG. 5, also employs a loop conductor 34-35 extending over the beveled surface portion of the distal tip but, rather than having a narrow trace connecting the loop conductor back to the proximal end of the blade blank, a generally wider trace as at 44 and 46 extend back to the proximal handle-receiving portion 12.

It should also be recongized that the optional overcoating discussed in connection with View E of FIG. 1 can be applied to the blades having the metallization patterns shown in FIGS. 3-6.

In each of the embodiments, because the working tip portion of the blade elements are tapered to a blunt edge, a high current density is developed at the tip for effecting tissue cutting. It has been found that a gap on the order of three mills between the tip metallization patterns provides optimum results. If too small a gap is provided for, a sufficiently high RF energy to part tissue cannot be maintained. If the gap becomes too large, i.e., the edge surface is too blunt, too high a voltage is needed to create an arc across the gap for cutting.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can he accomplished without departing from the scope of the invention itself.

What is claimed is:

1. A method of fabricating an electrosurgical blade comprising the steps of:
   (a) forming a thin, flat substrate of a desired shape from a ceramic material;
   (b) grinding a taper along a selected portion of the major surfaces of said substrate leading to the edge of said substrate;
   (c) depositing a pattern of metallization on each side pattern extending over the tapered portion; and
   (d) backgrinding the substrate to form a blunt edge surface face of metallization which extends between said tapered portions of said major surfaces.

2. The method as in claim 1 and further including the step of coating said blade with a high temperature insulating material exhibiting high electrical impedance.

3. The method as in claim 2 wherein said insulating material is selected from the group consisting of aluminum oxide, boron nitride, silicon dioxide, zirconium oxide, titanium nitride and silicon nitride.

* * * * *

UNITED STATES PATENT AND TRADEMARK OFFICE
CERTIFICATE OF CORRECTION

PATENT NO. : 4,958,539
DATED : September 25, 1990
INVENTOR(S) : Peter Stasz, et al.

It is certified that error appears in the above-indentified patent and that said Letters Patent is hereby corrected as shown below:

Column 6, line 7, change "face" to -- free --.

Signed and Sealed this

Third Day of May, 1994

Attest:

BRUCE LEHMAN

Attesting Officer      Commissioner of Patents and Trademarks